United States Patent [19]

Weidmann et al.

[11] Patent Number: 4,645,350
[45] Date of Patent: Feb. 24, 1987

[54] DENSITOMETER

[75] Inventors: Markus Weidmann, Niederglatt; Hans Ott, Regensdorf; Wilhelm H. Koch, Otelfingen, all of Switzerland

[73] Assignee: Gretag Aktiengesellschaft, Regensdorf, Switzerland

[21] Appl. No.: 763,700

[22] Filed: Aug. 8, 1985

[30] Foreign Application Priority Data

Aug. 8, 1984 [CH] Switzerland ........................ 3802/84

[51] Int. Cl.⁴ .......................... G01J 3/51; G01N 21/47
[52] U.S. Cl. .................................... 356/418; 356/446
[58] Field of Search ............... 356/404, 406, 416, 418, 356/419, 443, 444, 445, 446

[56] References Cited

U.S. PATENT DOCUMENTS 3,734,630 5/1973 McIntosh et al. .................. 356/444
3,771,877 11/1973 Rosencranz ......................... 356/416
4,053,235 10/1977 Hampton et al. .................... 356/418

Primary Examiner—F. L. Evans
Attorney, Agent, or Firm—Burns, Doane, Swecker & Mathis

[57] ABSTRACT

A densitometer is described which is equipped with an extendable and retractable measuring head driven by an electric motor. In the retracted rest position, a measuring diaphragm is visible to the user and the instrument may be positioned. In the extended working position the measuring head covers the measuring diaphragm. By means of the electric drive of the measuring head, the risk of erroneous positioning is avoided.

8 Claims, 11 Drawing Figures

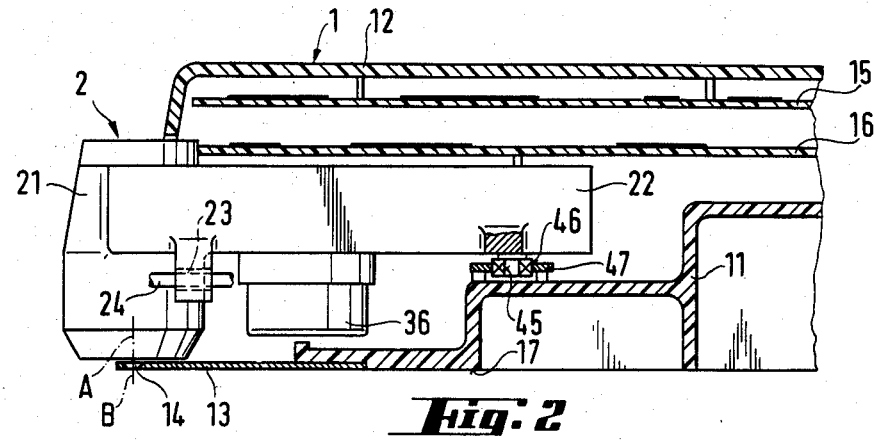
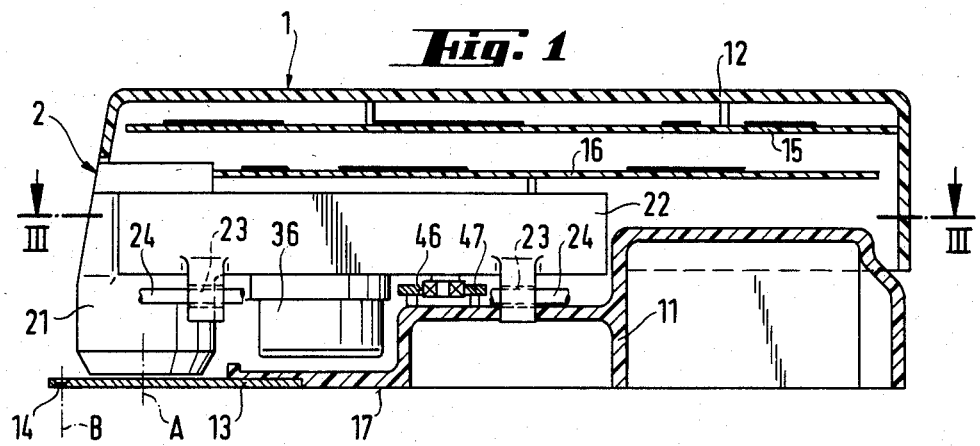
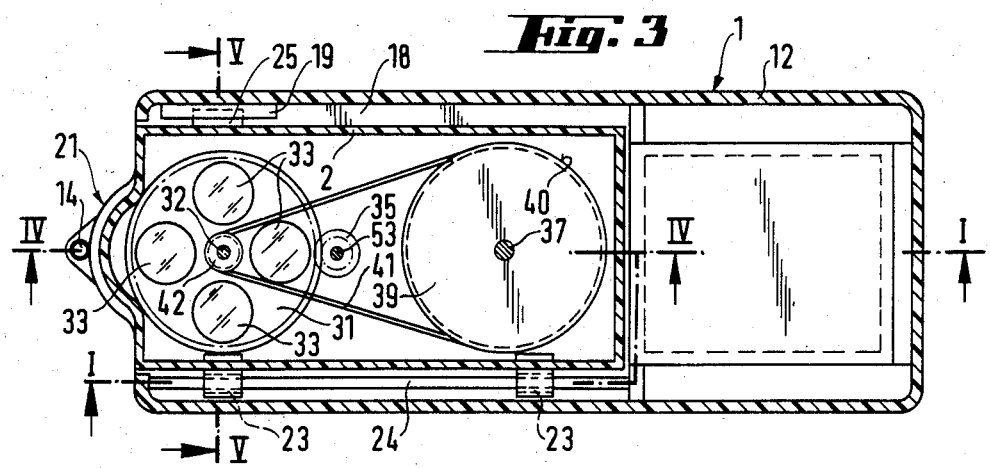

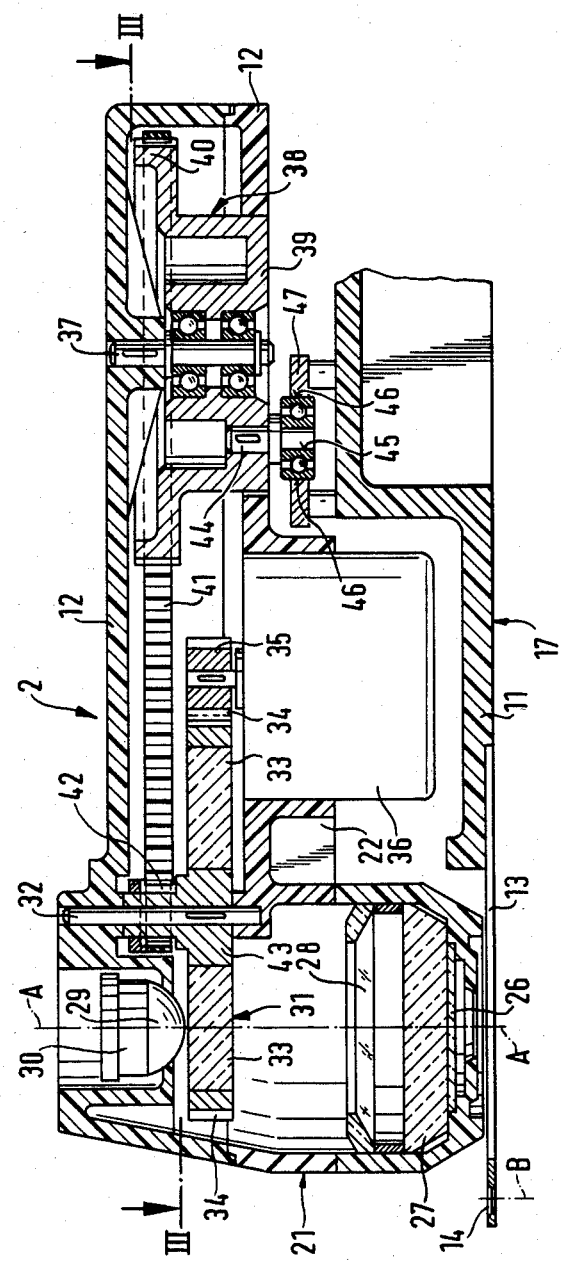

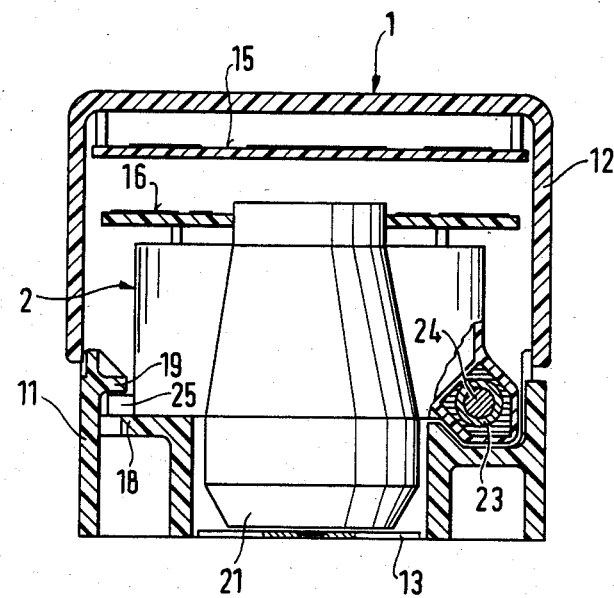

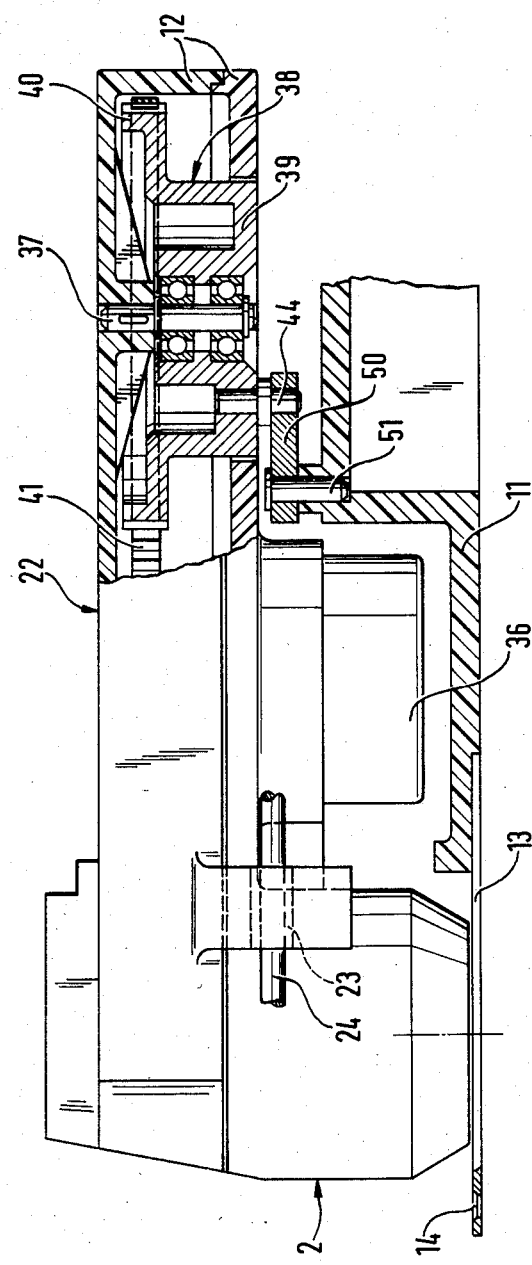

4,645,350

DENSITOMETER

FIELD OF THE INVENTION

The invention concerns a densitometer of the type having a flat measuring surface resting on a flat support surface and wherein a measuring head is displaceable in the densitometer housing. The measuring head is movable from a rest position, in which a measuring diaphragm visible to the user serves to position the densitometer on the measuring surface, to a working position, in which the measuring head covers the measuring diaphragm.

BACKGROUND OF THE INVENTION

Practically all of the manual densitometers available at the present time are equipped with a more or less elaborately designed measuring head lowering device, which makes it possible to bring the measuring head from a rest position in which the instrument may be positioned in the location desired, into a working position wherein the measuring process takes place. Obviously, the measuring head must be moved in the process at a greater or lesser distance from the support carrying the object of the measurement, and parallel to it. With the known densitometers this always requires the actuation of a handle or at least the application of a force in a direction parallel to the support, frequently resulting in an unintentional displacement of the densitometer, which in view of its slight extent often remains undetected. This may lead to incorrect positioning and thus to erroneous measurements.

U.S. Pat. No. 3,734,630 describes a special densitometer suitable for manual operation and equipped with a measuring head displaceable parallel to the support surface. The measuring head is driven by means of a linkage, not described in detail, by the application of pressure perpendiculary to the support surface to a yoke in the housing, again not explained in detail. In the case of this densitometer the risk of positioning errors is somewhat less, but it remains capable of improvement in many respects. In particular, the primitive drive of the measuring head indicated is not free of jolts and thus cannot provide the precision required at the present time, and furthermore, the densitometer is not suitable for measurements in several color channels.

Further photoelectric measuring instruments with moving measuring heads and other parts of the measuring setup are described in U.S. Pat. Nos. 3,535,046; 3,777,163; 4,173,416; 2,807,980 and 3,698,819. However, none of these references discloses a manual densitometer resembling the instrument according to the invention in any way.

OBJECTS AND SUMMARY OF THE INVENTION

The invention is intended to eliminate the above-described problem and to provide a manual densitometer that may be positioned without problems; and where there is no danger that the device will be displaced unintentionally on the support while being moved into its working position. In particular, the movement of the measuring head should be precise and without jolts and the equipment outlay required should be as low as possible.

An example of embodiment of a densitometer according to the invention is explained below with reference to the drawings. In the drawings:

BRIEF DESCRIPTION OF THE DRAWINGS

FIG. 1 shows a longitudinal section through the manual densitometer with the measuring head retracted;

FIG. 2 a partially cut longitudinal section similar to FIG. 1, but with the measuring head extended;

FIG. 3 a horizontal section approximately on the line III—III in FIG. 1;

FIG. 4 a longitudinal section through measuring carriage on the line IV—IV of FIG. 3;

FIG. 5 a vertical section through the densitometer approximately on the line V—V of FIG. 3;

FIG. 7 a view similar to FIG. 4 of an alternative embodiment.

DETAILED DESCRIPTION

Figure 6A:
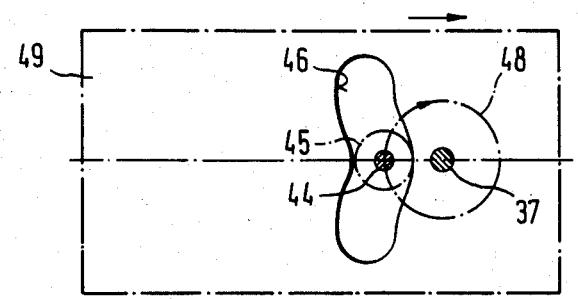
FIGS. 6a–6e are schematic illustrations to explain the drive of the measuring carriage.

The manual densitometer shown is of an essentially square external configuration. Its housing 1 consists of a bottom part 11 and a cover 12 mounted on it. Both parts are preferably made of a synthetic plastic material.

In the housing 1 a measuring carriage, designated in its entirety by 2, is arranged. It is located normally in the retracted rest position shown in FIG. 1 and may be extended for the operation of the manual densitometer into the working position shown in FIG. 2. In this position the axis A of the densitometer measuring head located in the measuring carriage is aligned with the axis B of a measuring diaphragm 14 in a sight plate 13.

The sight plate 13 and the lower limiting edge 17 of the bottom 11 of the housing are located in one plane and form a flat stand surface, whereby the densitometer is set onto the usually flat support carrying an object to be measured.

The housing 1 further comprises two printed circuit boards 15 and 16, carrying the electronic components (not shown) of the densitometer. The upper board 15 is mounted in the housing cover 12, while the lower board 16 is connected with the measuring carriage 2 and moves with it.

The densitometer shown is highly similar in its external appearance and with regard to its optical measuring equipment and electronics to the manual densitometer marketed by Gretag AG, Regensdorf, Switzerland, under the designated "D 142." The essential difference of the invention is in the extendable measuring carriage and its drive. The following description is thus essentially restricted to these parts.

The measuring carriage 2 consists of a tubular front part 21 and a square rear part 22. The first forms and comprises the measuring head itself, while the latter contains or carries the part required to drive the measuring carriage.

The measuring carriage 2, as mentioned above, is arranged displaceably in the densitometer housing. For this purpose, it is equipped laterally with two slide bushes 23, which slide on a guide rod 24 mounted in the bottom part 11 of the housing, thereby guiding the measuring carriage in a straight line. On the side opposite to the slide bushes 23 the measuring carriage 2 has a guide bead 25. The latter slides on a flange 18 forming a bearing surface molded onto the bottom part 11 of the housing and is held down by a guide rib 19 (see also FIG. 5).

In the tubular measuring head 21 of the measuring carriage 2 different lenses and other optical components 26–29 are located, together with a photodiode 30 as a photoelectric transformer. A filter wheel 31 is further provided; it may be rotated around an axle 32 so that its four measuring filters 33 may be introduced successively into the path of the measuring beam (FIG. 3, 4).

The filter wheel 31 carries external teeth 34, engaging the teeth of pinion gear 35 of a drive motor 36 mounted in the rear part 22 of the measuring carriage 2. A drive pulley 38 is supported rotatingly around an axle 37 at the rear end of the part 22 of the measuring carriage 2. It has a disk shaped center part 39 and a cylindrical toothed peripheral part 40 and is driven by a toothed belt 41 engaging its peripheral part 40, said toothed belt in turn being actuated by a toothed pulley 42 on the hub 43 of the filter wheel 31. The drive pulley 38 is therefore also driven by the motor 36. The gear ratio between the filter wheel 31 and the drive pulley 38 is approximately 1:7 and between the pinion gear of motor 36 and the filter wheel 31 approximately 1:5.

A shaft 44 is mounted eccentrically on the center part 39 of the drive pulley 38, with a sliding link in the form of a ball bearing 45 being in turn mounted on said shaft 44 in a freely rotating manner. The sliding link engages the guide slot 46 of the plate-shaped link 47 fastened to the bottom part 11 of the housing.

The shape of the guide slot 46 in the slotted link 47 and the mode of operation of the crank drive including the drive pulley 38, the slide link 45 and the slotted link 47 are schematically shown in FIGS. 6a–6e. In the figures, 48 indicates the circular path of the sliding link 45 during a complete rotation of the drive pulley 38 around the axle 37 and 49 identifies symbolically the measuring carriage 2.

Figure 6B:
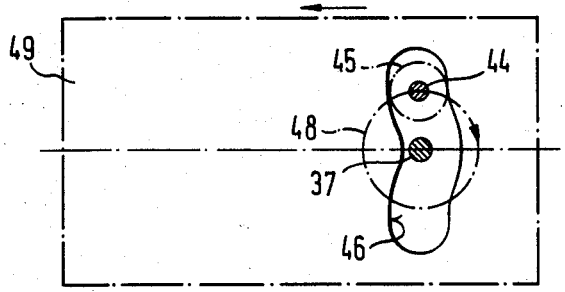
Figure 6C:
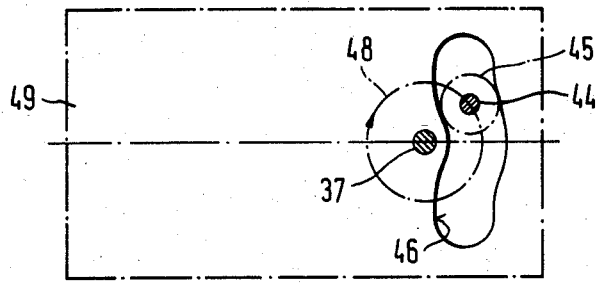
Figure 6D:
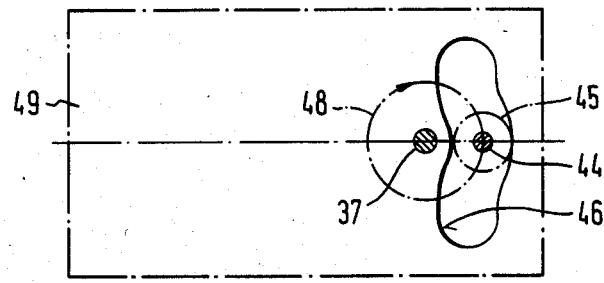
Figure 6E:
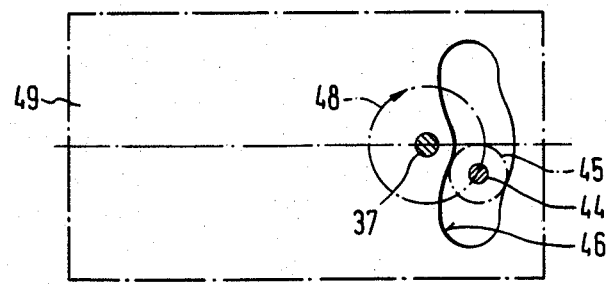

FIG. 6a shows the rest position wherein the measuring carriage 2 is completely retracted as shown in FIG. 1 or FIG. 4. The actuation of the motor 36 (by means of a switch, not shown) initiates a measuring cycle. The drive pulley 38 rotates in the direction of the arrow and thereby effects a displacement of the measuring carriage 2 toward the left (outline 49; FIGS. 6b, 6c). Following a rotation by approximately 135° of the drive pulley 38, the measuring carriage is fully extended and has attained its working position. Upon a further rotation of the drive pulley 38 to approximately 225° (FIG. 6e) the position of the measuring carriage remains practically constant as a result of the specific configuration of the guide slot in the slotted link. From the rotating position of approximately 135° to the rotating position of approximately 225°, i.e., during a quarter turn, the densitometric measure is effected (in a conventional manner), wherein due to the chosen gear ratio of the drive pulley 38 and the filter wheel 31, the latter performs two rotations and therefore two measurements may be performed with each filter 33. The measuring carriage 2 moves upon a further rotation of the drive pulley 38 back into its initial or rest position shown in FIG. 6a and the drive motor 36 is automatically deactivated.

The crank drive described above may be adapted in an optimum manner to the specific conditions of a densitometer by the corresponding configuration of the slot 46. In particular, jolt free motion may be obtained at relatively high velocities and the stopping period of the measuring head may be chosen in an extensively free manner.

A somewhat simpler drive with fewer degrees of freedom may be otained according to FIG. 7. Here, a push rod 50 is supported rotatingly on the eccentric shaft 44 in the center part 39 of the drive pulley 38. The other end of push rod 50 is rotatably fastened by means of a journal 51 to the bottom part 11 of the housing. This kinematic layout provides a sinoidal movement path with velocities being lowest near the two extreme positions.

Further variation of the drive will readily occur to those skilled in the art. For example, it is conceivable to provide a separate drive for the filter wheel or to eliminate the drive motor entirely, whereupon the measuring carriage would be moved manually. In this case, however, it would be necessary to insure, by means of suitable reversing kinematics, that the external force effecting the drive would be applied only perpendicularly to the support surface (no slipping) and that this force would be then deflected correspondingly in a direction parallel to the support surface.

What is claimed is:

1. A densitometer, comprising:
    a housing having a flat support surface and adapted to rest on a flat measuring surface;
    a measuring carriage movably mounted in said housing;
    a measuring head mounted on said carriage and movable therewith;
    a drive motor mounted on said carriage and movable therewith;
    means connected to said drive motor for moving said carriage so that said measuring head moves to and from a rest position to a working position, said means disposed so that said measuring head remains essentially motionless in the working position with the drive motor running; and
    a measuring diaphragm connected to said housing for positioning said housing on said measuring surface, said measuring diaphragm being visible to a user in the rest position of said measuring head, but being covered by said carriage in the working position of said measuring head.

2. A densitometer as set forth in claim 1, wherein the measuring head includes:
    a rotatable filter wheel having a plurality of different measuring filters disposed therein; and
    means connected to said filter wheel for causing rotation of said filter wheel by said drive motor.

3. A densitometer as set forth in claim 2, wherein said means connected to said filter wheel causes the filter wheel to perform at least one complete rotation during a measuring period.

4. A densitometer as set forth in claim 1, and further comprising:
    a slotted follower element disposed on said carriage for being driven by said drive motor over a circular path; and
    a stationary slotted link mounted on said housing.

5. A densitometer, as set forth in claim 1, and further including:
    a slide rod fastened to said housing; and
    means on said carriage for guiding said carriage along said slide rod.

6. A densitometer, as set forth in claim 2, and further including:
    a slide rod fastened to said housing; and
    means on said carriage for guiding said carriage along said slide rod.

7. A densitometer, as set forth in claim 3, and further including:

a slide rod fastened to said housing; and means on said carriage for guiding said carriage along said slide rod.

8. A densitometer, as set forth in claim 4, and further including:
a slide rod fastened to said housing; and
means on said carriage for guiding said carriage along said slide rod.

* * * * *